United States Patent [19]

Lafon

[11] Patent Number: 4,755,522
[45] Date of Patent: Jul. 5, 1988

[54] DERIVATIVES OF N-[3-(2,4,6-TRIMETHOXYBENZOYL)-PROPYL]PIPERIDINE, AND THEIR USE IN THERAPEUTICS

[75] Inventor: Louis Lafon, Paris, France

[73] Assignee: Laboratoire L. Lafon, Maisons-Alfort, France

[21] Appl. No.: 42,298

[22] Filed: Apr. 24, 1987

[30] Foreign Application Priority Data

Apr. 28, 1986 [FR] France .................................. 86 06133

[51] Int. Cl.$^4$ .................... A61K 31/445; C07D 211/32
[52] U.S. Cl. ...................................... 514/330; 514/317; 546/237; 546/238
[58] Field of Search ................ 546/238, 237; 514/330, 514/317

[56] References Cited

U.S. PATENT DOCUMENTS 3,895,030 7/1975 Lafon .................................. 546/237
4,705,795 11/1987 Lafon .................................. 514/317

FOREIGN PATENT DOCUMENTS 1183853 3/1985 Canada ................................ 546/237
0063075 10/1982 European Pat. Off. ............ 546/237
2101045 3/1972 France ................................. 546/237

Primary Examiner—Robert T. Bond
Attorney, Agent, or Firm—Wegner & Bretschneider

[57] ABSTRACT

This invention is drawn to compounds of the formula:

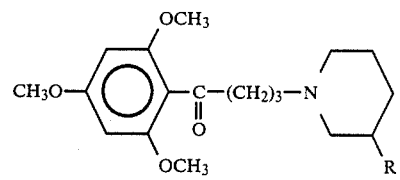

in which R is —CH$_2$OH, —COOH and —COOR$_1$, R$_1$ being a C$_1$ to C$_4$ alkyl group, and their pharmaceutically acceptable salts. The compounds of the invention are useful as anti-depressants and as anti-arrhythmics.

5 Claims, No Drawings

DERIVATIVES OF N-[3-(2,4,6-TRIMETHOXYBENZOYL)PROPYL]-PIPERIDINE, AND THEIR USE IN THERAPEUTICS

DESCRIPTIVE SUMMARY

The subject of the invention is compounds with the formula:

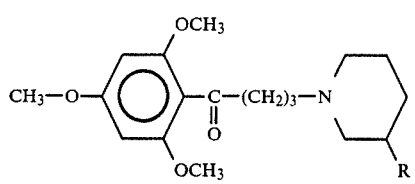

in which R is chosen from the groups —CH$_2$OH, —COOH and —COOR$_1$, R$_1$ being a C$_1$ to C$_4$ alkyl group, and their pharmaceutically acceptable salts.

These compounds are useful in therapeutics.

The present invention is concerned with new derivatives of N-[3-(2,4,6-trimethoxybenzoyl)propyl]piperidine, their preparation processes and their use in therapeutics.

A certain number of derivatives of N-[3-(2,4,6-trimethoxybenzoyl)propyl]piperidine or of similar compounds have already been described:

U.S. Pat. No. 3,895,030 describes in particular (2,4,6-trimethoxyphenyl) (3-pyrrolidinopropyl) ketone (Buflomedil) which is a peripheral vasodilator agent marketed under the name of Fonzylane, and (2,4,6-trimethoxyphenyl) (3-piperidinopropyl) ketone, which offers an antispasmodic activity.

Patent FR-A-2 404 003 describes (hydroxyphenyl) (3-pyrrolidinopropyl) ketones which possess a vasodilatory activity.

Patent FR-A-2 534 912 describes derivatives of (2,4,6-trimethoxyphenyl) (3-piperidinopropyl) ketone and in particular (2,4,6-trimethoxyphenyl)-[3-(3-methylpiperidino)propyl] ketone (CRL 41034) which possesses vasodilatory and hypotensive properties.

Patent GB-A-1 115 992 describes N-(4'-methylpiperidino) 2,4,6-trimethoxy acetophenone which offers an antispasmodic, tranquilizing and analgesic activity.

The Applicant has found a new class of derivatives of N-[3-(2,4,6-trimethoxybenzoyl)propyl]piperidine which offer original pharmacological activities which can be used in therapeutics.

The subject of the present invention is thus compounds with the formula:

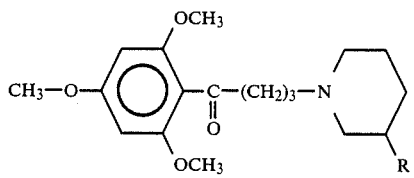

in which R is chosen from the groups —CH$_2$OH, —COOH and —COOR$_1$, R$_1$ being a C$_1$ to C$_4$ alkyl group,
and their pharmaceutically acceptable salts.

The present invention concerns more particularly N-[3-(2,4,6-trimethoxybenzoyl)propyl]piperidine-3-methanol and its pharmaceutically acceptable salts which are characterized by an anti-arrhythmic activity.

The subject of the present invention is also therapeutic compositions containing, as active principle, a compound with the formula (I) or one of its pharmaceutically acceptable salts.

By pharmaceutically acceptable salts, one means addition salts that the compounds with the formula (I) form with pharmaceutically acceptable acids, as well as the salts that the compounds with the formula (I) with an acid group form with pharmaceutically acceptable bases.

"Addition salts with pharmaceutically acceptable acids" means salts which give the biological properties of free bases, without having an undesirable effect. These salts can be in particular those formed with mineral acids, such as hydrochloric acid, hydrobromic acid, sulphuric acid, nitric acid and phosphoric acid; acid metallic salts, such as disodium orthophosphate and monopotassium sulphate, and organic acids, such as the following acids:- formic, acetic, propionic, glycolic, oxalic, fumaric, lactic, succinic, tartaric and pamoic.

Likewise, "salts with pharmaceutically acceptable bases" means salts which do not modify the biological properties of free acids. These salts can be in particular those formed with mineral bases, such as sodium hydroxide, potassium hydroxide, lithium hydroxide, calcium hydroxide, and magnesium hydroxide, or organic bases such as glucamine, N-methyl-glucamine, N,N-dimethyl-glucamine, ethanolamine, diethanolamine, morpholine, N-methyl morpholine, tris-(hydroxymethyl)-methylamine and lysine.

The compounds according to the present invention can be obtained by condensation of a compound with the formula:

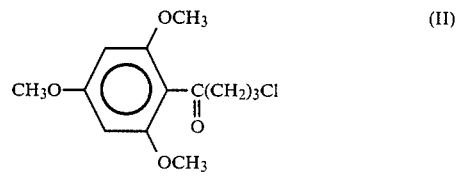

with a piperidine with the formula:

This reaction can be carried out in an organic solvent such as toluene in the presence of an excess of the compound with the formula (III).

The compound with the formula (II) can be obtained by a Friedel and Crafts reaction between phloroglucinol trimethyl ether and ω-chlorobutyryl chloride.

As a variation the compounds with the formula (I) can be obtained by condensation of a butyronitrile with the formula:

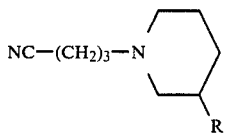

(IV)

with phloroglucinol trimethyl ether, according to a Houben-Hoesch reaction, in the presence of hydrochloric acid without a catalyst, and subsequent acid hydrolysis.

Butyronitriles with the formula (IV) can be obtained by condensation of 4-chlorobutyronitrile with a piperidine with the formula (III) in a solvent such as toluene.

The following examples illustrate the preparation of the compounds with the formula I.

EXAMPLE 1

Preparation of N-[3-(2,4,6-trimethoxybenzoyl)propyl]-3-piperidinemethanol hydrochloride (code no. CRL 41 391)

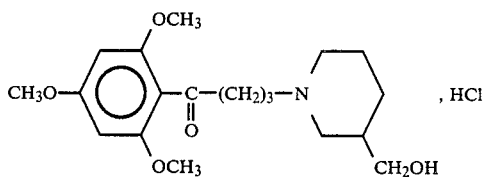

(a) Preparation of 1-(2,4,6-trimethoxybenzoyl)-1-chloropropane

Over 1 hour 30 min. a solution of 60.5 g (0.232 mole) of stannic chloride in 75 ml of benzene is poured into a solution maintained at about 5° C. of 33.6 g (0.200 mole) of 1,3,5-trimethoxybenzene and of 30.5 g (0.216 mole) of 4-chlorobutyryl chloride in 150 ml of benzene, with agitation for 3 hours at ambient temperature. The reactional medium is poured on to 250 ml of iced 4N hydrochloric acid and the organic phase is decanted.

After drying on dry sodium sulphate and evaporation of the solvent, 55 g of an orange-coloured oil is obtained. Yield, 100%.

(b) Preparation of N-[3-(2,4,6-trimethoxybenzoyl)propyl-3-piperidinemethanol hydrochloride Over 1 hour, a solution of 27.25 g (0.01 mole) of the product obtained at a) in 20 ml of toluene is poured into a solution at reflux of 23 g (0.20 mole) of 3-piperidine methanol in 60 ml of toluene, and the reflux is maintained for 1 hour 30 minutes. The reactional medium is washed with water and extracted with N hydrochloric acid. After alkalizing the aqueous phase with 4N sodium hydroxide, 27.8 g of an orange-coloured oil is isolated.

This oil is treated in ethyl ether with hydrochloric ethanol and the precipitate obtained is purified by crystallization from an acetonitrile/isopropanol mixture (9/1), to give 20 g of a slightly beige-coloured powder soluble in water. m.p. inst. (Kofler)=177° C. Yield=51.6%.

EXAMPLE 2

Preparation of ethyl N-[3-(2,4,6-trimethoxybenzoyl)propyl] nipecotate hydrochloride (Code no. CPL 41 389)

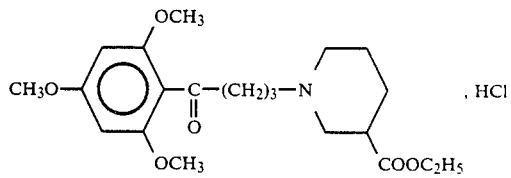

Over 1 hour, a solution of 27.25 g (0.10 mole) of the product obtained at example 1a, in 20 ml of toluene is poured into a solution at reflux of 31.4 ml, (0.20 mole) of ethyl nipecotate in 60 ml of toluene and the reflux is continued for 3 hours. The reactional medium is washed with water and extraction is done with an N solution of hydrochloric acid. After alkalizing with sodium carbonate, the aqueous phase liberates 31.4 g of a slightly green oil.

This oil is treated in ethyl ether with hydrochloric ethanol and the precipitate obtained is purified by two successive crystallizations with treatment by black 3 S in an ethyl acetate/ethanol mixture (3/1) and acetonitrile to give 12 g of a white powder soluble in water. m.p. inst. (Kofler)=155° C. Yield=27.9%.

EXAMPLE 3

Preparation of N-[3-(2,4,6-trimethoxybenzoyl)propyl]-3-piperidine carboxylic acid hydrochloride (Code no. CRL 41 390)

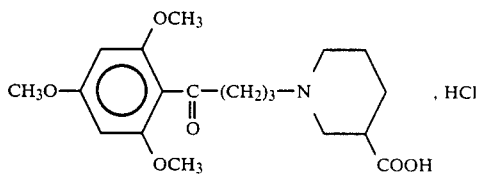

(a) Preparation of ethyl N-(3-cyanopropyl) nipecotate

Over 1 hour, 32.9 g (0.318 mole) of 4-chlorobutyronitrile is poured into a solution at reflux of 100 g (0.636 mole) of ethyl nipecotate in 80 ml of toluene in the presence of a trace of potassium iodide, and the reflux is continued for a further 2 hours. The reactional medium is diluted with ethyl ether, the precipitate is eliminated by filtering and the filtrate is washed with water.

After drying and evaporation of the solvent, the residue is purified by distilling under reduced pressure, to give 50.8 g of a colourless oil.

b.p.$_{5\ mm}$=152°–154° C. Yield=71.1%.

(b) Preparation of N-[3-(2,4,6-trimethoxybenzoyl)propyl]-3-piperidine carboxylic acid hydrochloride Over 3 hours and at about 0° C., a solution of 16.8 g (0.10 mole) of 1,3,5-trimethoxybenzene and 22.4 g (0.10 mole) of the product obtained at a) in 120 ml of anhydrous chlorobenzene are saturated by a current of hydrochloric acid. The rose-coloured gelatinous mass is extracted by water, the aqueous phase is taken to reflux for 1 hour, and then taken to dryness under reduced pressure. The residue is dried by azeotropic distillation in benzene and the precipitate obtained is isolated by filtering.

This product is purified by two successive crystallizations from absolute ethanol, then from an acetonitrile/methanol (9/1) mixture, to give 13 g of a white powder, soluble in water and in sodium hydroxide. m.p. about 190° C. Yield 32.4%. Total yield, 23%.

Results of the pharmacological studies are given below.

(1) Compound of example 1 (CRL 41,391)

(a) Acute toxicity

| Dose I.P. mg/kg | Mortality/6 mice |
| --- | --- |
| 195 | 0 |
| 232.5 | 3* |
| 260 | 5* |
| LD$_{50}$/232 mg/kg | |

*convulsions.

(b) Action on the cardio-vascular system (in the dog).

3 dogs (average weight, 12 kg) anaesthetized with nembutal, receive the compound by intra-duodenal route at successive doses of 0.1–0.5–2.5–10 and 20 mg/kg.

The arterial pressure, the cardiac rate, the femoral arterial flow, the vertebral arterial flow, the rectal and skin temperatures are all measured. The coloration of the skin is observed.

The compound has no effect on the arterial pressure. It increases the femoral flow, starting at a dose of 5 mg/kg, and reduces the vertebral flow. At 20 mg/kg, it slightly reduces the heart rate. It does not modify the rectal and cutaneous temperatures.

The effects on the arterial pressure and on the cardiac rate of isoprenaline tested after the accumulated dose of 39.1 mg/kg of the compound I.D. are very slightly reduced; at 10 mcg/kg of isoprenaline intravenously, the diastolic arterial pressure changes after the product from 107 to 36 mmHg (71, and in the control from 120 to 37 mmHg (83), while the cardiac rate changes after the product from 160 to 255 beats/minute and in the control from 157 to 273 beats/minute. The hypertension with noradrenaline is slightly reduced; at 2 mcg/kg intravenously of noradrenaline, the systolic pressure changes after the product from 149 to 256 mmHg, and from 153 to 271 mmHg in the control.

Two of these three dogs having undergone a ligature of a coronary artery a few weeks earlier still presented numerous ectopic heart-beats. The compound re-established a normal rhythm in these two dogs at 2.5 mg/kg for one and 10 mg/kg for the other.

In the third dog, arrhythmias were caused by injection of adrenaline (10 mcg/kg), preceded by an intra-trachealinjection of petroleum ether (0.1 ml/kg before and after administration of the 39.1 mg/kg (in cumulative doses) of the compound. On the E.C.G., the number of beats of sinusoidal origin and the number of ectopic beats per minute are counted which follow the injection of adrenaline.

| Dose of compound | Number of beats in 1 minute | |
| --- | --- | --- |
| mg/kg I.D. | ectopic | sinusoidal |
| 0 | 163 | 35 |
| 39.1 | 26 | 173 |

The compound strongly reduces the number of ectopic beats caused by adrenaline+petroleum ether.

In a dog of which the left descending coronary artery had been ligatured 24 hours earlier, the compound was administered by intravenous route at increasing doses: 0.5–1–2.5–5–10 mg/kg. every 30 minutes.

The number of beats of sinusoidal origin, zero in the control, increased progressively starting at a dose of 2.5 mg/kg. 5%+ of sinusoidal beats at this dose, 19% at 5 mg/kg, 5 minutes after the injection. 41%, 20 minutes after the injection. 25% at 40 minutes and 15% at 60 minutes.

At the same time, the compound moderately decreases the cardiac frequency which passes from 231 to 174 beats/minute, or −25% after a dose of 10 mg/kg, and at this dose brings on brief vomitting.

4 days after the ligature of the coronary, this same dog received injections I.V. of 5 mcg/kg of adrenaline which caused arrhythmias. The number of ectopic beats caused by adrenaline reduces starting from the dose of 5 mg/kg I.V. while the percentage of ectopic beats referred to the total cardiac frequency is 79% in comparison with 100% in the control and 46% 10 minutes after the dose of 10 mg/kg (64% after 40 minutes, 88% after 90 minutes).

In order to determine the distance between the anti-arrhythmic dose and the dose causing the toxic effects, an awakened dog received the compound by intravenous route every 45 minutes, 5 times at a dose of 10 mg/kg plus one dose of 20 mg/kg, i.e., a total dose of 70 mg/kg I.V. The dog vomited after 40 mg/kg and 70 mg/kg, 5 minutes after the injection: the nictitating membrane was released for 10 minutes at 70 mg/kg; a certain somnolence was observed in this animal.

(c) Anti-arrhythmic action in the mouse.

Research on the anti-arrhythmic activity by intraperitoneal route on Lawson's test in mice (ventricular fibrillation (V.F.) by inhalation of chloroform, all or nothing response) has given the following results (10 mice per dose).

| Dose mg/kg I.P. | % of mice not presenting V.F. |
| --- | --- |
| 0 | 0 |
| 5 | 22 |
| 10 | 50 |
| 20 | 70 |

(d) Anti-arrhythmic action in the guinea-pig.

The compound was administered by intravenous route at a dose of 10 mg/kg to a series of 10 albino guinea-pigs of 380 to 495 g, anaesthetized with urethane.

5 minutes later, they receive an I.V. perfusion of the product causing arrhythmia at a dosage of 0.09 mg/min. in a volume of 0.6 ml/min.

The compound is compared with quinidine at a dose of 5 mg/kg I>V> and with a series of controls.

Lots are drawn for the treatments.

A—Action on arrhythmias with K-strophanthin.

At a dose of 10 mg/kg I.V., the compound significantly delays the appearance of incidents in the E.C.G. due to the K-strophanthin except that of the 1st extra systole.

It does not significantly modify the cardiac frequency.

B—Action on arrhythmias with aconitine.

At a dose of 10 mg/kg I.V., the compound significantly retards the appearance of incidents in the E.C.G. due to aconitine. In this animal group, at a dose of 10 mg/kg I.V., the compound increases the cardiac frequency by an average of 12 beats/minute (tachycardia in 6 animals/10).

At a dose of 5 mg/kg I.V., quinidine significantly retards only the appearance of ventricular tachycardia. This retardation (+30% on the average) is significantly less than that observed with the compound according to the invention.

C—Conclusion.

The compound CRL 41,391, administered at a dose of 10 mg/kg I.V. to the anaesthetized guinea-pig significantly delays the appearance of incidents in the E.C.G. caused by K-strophanthin and aconitine, without modifying or with very moderate increase in the cardiac frequency.

Its action as compared with aconitine is greater than that observed after pre-treatment with 5 mg/kg of quinidine.

It thus appears that the compound promises to be a femoral vasodilator product possessing useful anti-arrhythmia properties effective at a dose weak compared with the toxic dose.

(2) Compound of Example 2 (CRL 41,389)

The compound of example 2 in solution in distilled water (pH 5.5 to 6.0) was administered by intraperitoneal route at a rate of 20 ml/kg in mice (male, NMRI, C.E.R. January) and of 5 ml/kg to rats (male, $CD_1$, Sprague Dawley, Charles River).

Pre-toxicity 128 mg/kg (3 mice)—sedation and reduction of respiratory frequency for 5 minutes. No mortality.

256 mg/kg (6 mice)—sedation and reduction of respiratory frequency, convulsions (2/6), mortality (1/6), 5 minutes after the injection.

512 mg/kg (6 mice)—reduction of respiratory frequency, convulsions (5/6). Mortality (3/5), 5 minutes after injection.

1024 mg/kg (6 mice)—convulsions, reduction of the respiratory frequency. Mortality (3/3), 4 minutes after injection.

The compound CRL 41,389 causes a moderate potentialization of the amphetaminic stereotypies in the rat, a reduction of intergroup aggressivity and an aggravation of reserpinic hypothermia.

On the cardiological plane, the compound, starting at a dosage of 2.5 mg/kg, I.V., reduces arrhythmias caused by I.V. injection of adrenaline in dogs of which the coronary artery has previously been ligatured.

In man, the compound is an anti-depressant stimulant.

(3) Compound of example 3 (CRL 41,390)

The sub-acute toxicity of the CRL 41,390 is similar to that of the CRL 41,389.

3 dogs (average weight, 14 kg) anaesthetized with nembutal, received the CRL 41,390 by intra-duodenal route, at successive doses of 0.1–0.5–1–2.5–5–10–20 mg/kg, then a supplementary dose of 10 mg/kg I.V.

The arterial pressure, the cardiac frequency, the femoral arterial flow, the vertebral arterial flow, the rectal and cutaneous temperatures, were measured. The coloration of the skin was observed.

The CRL 41,390 has no effect on the arterial pressure; it significantly reduces the heart rate from an IV dose of 2.5 mg/kg and an intraduodenal route of 20 mg/kg. A slight increase in the femoral flow is observed at the strong dose (20 mg/kg) particularly in a dog and a reduction in the vertebral flow. The rectal and cutaneous temperatures are moderately reduced.

The effects of isoprenaline on the diastolic arterial pressure and the cardiac frequency are slightly reduced: at 10 mcg/kg of isoprenaline, the diastolic arterial pressure passes, after administration of the product, from 131 to 44 mmHg/135 to 35 mmHg in the control, and the cardiac frequency passes after the product from 148 to 250 beats/min., 185 to 272 beats/min. in the control.

Hypertension to noradrenaline is not modified: at 2 mcg/kg of noradrenaline, the systolic arterial pressure passes, after administration of the product, from 160 to 290 mmHg/161 to 289 mmHg in the control.

Furthermore, the CRL 41,390 has no anti-arrhythmic action on the awakened dog.

It appears that the compounds according to the invention possess unexpected properties as compared with the compound of the prior technique which can be considered as the nearest, namely compound CRL 41,034.

In fact, the compounds according to the invention have no effect on the arterial pressure, while the CRL 41,034 has a hypotensive effect.

The compound of example 1 in the form of capsules or tablets with doses of 200 mg, 3 to 4 per day, has given good results in the treatment of cardiac arrhythmias in man.

The therapeutic compositions according to the invention can be administered to man or to animals by oral or parenteral route.

They can be in the form of solid, semi-solid or liquid preparations. For example, there can be mentioned tablets, capsules, suppositories, injectable solutions or suspensions, as well as the retardation forms and the slow-release implantation forms.

In the compositions, the active principle is generally mixed with one or more of the usual pharmaceutically acceptable excipients well known to the expert.

The quantity of the active administered obviously depends on the patient treated, on the administration route and on the severity of the illness.

What is claimed is:

1. A compound of the formula:

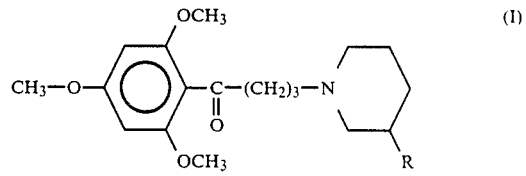

(I)

wherein R is selected from the group consisting of —CH₂OH, —COOH and COOR₁ groups, R₁ being $C_1$ to $C_4$ alkyl and a pharmaceutically-acceptable salt.

2. N-[3-(2,4,6-trimethoxybenzoyl)propyl]piperidine-3-methanol or a pharmaceutically-acceptable salt thereof.

3. An anti-depressant composition containing an effective anti-depressant amount of a $C_1$–$C_4$ alkyl ester of N-[3-(2,4,6-trimethoxybenzoyl)propyl] nipecotate or a pharmaceutically acceptable salt thereof and a therapeutically acceptable excipient.

4. An anti-arrhythmic composition having an anti-arrhythmic activity containing an effective amount of N-[3-(2,4,6-trimethoxybenzoyl)propyl] piperidine-3-methanol or a pharmaceutically acceptable salt thereof and a therapeutically acceptable excipient.

5. A method for the treatment of arrhythmia which comprises administering to a human in need thereof an effective amount of N-[3-(2,4,6-trimethoxybenzoyl)propyl] piperidine-3-methanol or a pharmaceutically acceptable salt thereof.

* * * * *